United States Patent
Suzuki et al.

(10) Patent No.: US 7,220,250 B2
(45) Date of Patent: May 22, 2007

(54) URINE RECEIVER AND URINE COLLECTION PROCESSING SYSTEM IMPLEMENTING URINE RECEIVER

(75) Inventors: Miou Suzuki, Kagawa-ken (JP); Ichiro Wada, Kagawa-ken (JP); Ryosuke Miyagawa, Tokyo (JP); Yoshikazu Ishitsuka, Ibaraki (JP); Nobuaki Yoshioka, Tokyo (JP); Junichi Kobayashi, Tokyo (JP); Shigeru Machida, Tokyo (JP)

(73) Assignees: Uni-Charm Corporation, Ehime-ken (JP); Hitachi, Ltd., Tokyo (JP)

( * ) Notice: Subject to any disclaimer, the term of this patent is extended or adjusted under 35 U.S.C. 154(b) by 0 days.

(21) Appl. No.: 11/179,778

(22) Filed: Jul. 13, 2005

(65) Prior Publication Data

US 2006/0015081 A1    Jan. 19, 2006

(30) Foreign Application Priority Data

Jul. 15, 2004    (JP) ............................... 2004-209268

(51) Int. Cl.
*A61M 1/00*    (2006.01)
(52) U.S. Cl. ....................................... 604/317; 604/328
(58) Field of Classification Search ................ 604/317, 604/328–331, 346–347, 354, 356
See application file for complete search history.

(56) References Cited

U.S. PATENT DOCUMENTS 4,747,166 A * 5/1988 Kuntz ........................ 4/144.1
5,678,564 A    10/1997 Lawrence et al.

FOREIGN PATENT DOCUMENTS

| EP | 1 112 728 | 7/2001 |
|---|---|---|
| EP | 1 457 178 | 9/2004 |
| EP | 1 486 184 | 12/2004 |
| GB | 2 244 653 | 12/1991 |
| JP | 05-123350 | 5/1993 |
| JP | 07-171182 | 7/1995 |
| JP | 07-239990 | 9/1995 |
| JP | 8-510924 | 11/1996 |
| JP | 11-113946 | 4/1999 |
| JP | 11-178849 | 7/1999 |
| JP | 2001-276108 | 10/2001 |
| JP | 2002-311025 | 10/2002 |

* cited by examiner

*Primary Examiner*—Michele Kidwell
(74) *Attorney, Agent, or Firm*—Lowe Hauptman & Berner LLP

(57) ABSTRACT

A urine receiver which is sanitary, easy to attach, and furthermore, prevents urine leakage even when a wearer repeatedly changes positions is provided. A urine receiver 10 is implemented in a urine collection processing system wherein urine discharged from the wearer is suctioned into a urine tank via a urethral tube. The urine receiver 10 comprises, at the least: a liquid permeable, air-impermeable sheet 21 which is placed opposite of and covering the urethral meatus of the wearer; a leak-proof sheet 22 which is placed on the surface of the air-impermeable sheet 21 opposite to the urethral meatus and bonds to the outer border of the air-impermeable sheet 21; a suction part 26 which is provided between the air-impermeable sheet 21 and the leak-proof sheet 22 and to which the urethral tube 11 is connected; and a gathers part 16 for sealing the space between the air-impermeable sheet 21 and the wearer's skin surface which is provided on the outer border part of the air-impermeable sheet 21 on the urethral meatus side.

14 Claims, 12 Drawing Sheets

(a)

(b)

URINE RECEIVER AND URINE COLLECTION PROCESSING SYSTEM IMPLEMENTING URINE RECEIVER

CROSS-REFERENCE TO RELATED APPLICATION

This application is based upon and claims the benefits of priority from Japanese Patent Application No. 2004-209268 filed on Jul. 15, 2004, the entire contents of which are incorporated herein by reference.

FIELD OF THE INVENTION

The present invention is related to a urine tank for collecting urine discharged from a wearer and a urine collection processing device comprising this urine tank, which can, for example, assist people such as the elderly, hospitalized patients, and the physically disabled in urination.

RELATED ART

Conventionally, there are instances wherein it is difficult for hospitalized patients, physically disabled persons and others to control urination at will. In these instances, urine collection processing devices are used as devices to assist in urination.

The urine collection processing devices, for example, comprise a urine receiver for receiving urine which has been discharged, a urine tank which is connected to this urine receiver via a urethral tube, a urine detection sensor which is provided within the urine receiver, and a pump mechanism for pumping urine within the urine receiver to the urine tank via the urethral tube when urine is detected by the urine detection sensor (Patent References 1 to 4).

A cup-shaped urine receiver which is hollow on the inside is described in Patent References 1 and 2. A urethral tube is connected to this urine receiver and the receiver is placed so as to cover the outer urethral meatus by a supporter or the like. According to this construction, discharged urine is collected within the urine receiver, and the collected urine is suctioned from the end of the urine tube.

A urine receiver which has a boat-shaped pudenda component covered by flexible material with water-resistant features and a thick water-absorbent sheet which absorbs urine embedded within this pudenda component is described in Patent Reference 3. The inner surface of this pudenda component is coated with permeable sheet and is partitioned into a urine reception part and a feces reception part by a partition component.

A bag-shaped urine receiver is described in Patent Reference 4. The section of the outer surface of this urine receiver which contacts the wearer's skin has a permeable contact surface. The interior of the urine receiver is partitioned by water-resistant film and a urethral chamber, wherein a plurality of beads are stored, is provided. An opening which communicates with the urethral chamber within the urine receiver is provided on the contact surface.

[Patent Reference 1] JP, 11-113946, A

[Patent Reference 2] Japanese Unexamined Patent Publication No. 2001-276108

[Patent Reference 3] Japanese Patent No. 2563230

[Patent Reference 4] Japanese Patent No. 3137130

SUMMARY OF THE INVENTION

In the construction described in Patent References 1 and 2, however, urine within the urine receiver cannot be suctioned unless it is led to the vicinity of the end of the urethral tube. For this reason, if the wearer changes position, the urethral tube is not necessarily located in the section wherein urine is collected, and the risk of urine leaking arises while the wearer repeatedly changes position.

Therefore, if the urine receiver is fitted so as to press against the wearer in order to prevent urine from leaking out of the urine receiver, it must be fastened firmly with a supporter. In this case, not only does the wearer feel discomfort, but it is also difficult for the care-giver to attach the supporter onto the wearer.

In addition, in the construction described in Patent Reference 3, the thick water-absorbent sheet faces the urethral meatus of the wearer. Therefore, even if attempts are made to suction all of the urine collected in the urine receiver, urine remains within the thick water-resistant sheet and it becomes unsanitary.

Furthermore, because the urine receiver is divided into a urine reception part and a feces reception part, in actuality, the area of the urine reception part which receives urine is small and attaching the urine receiver troublesome.

In addition, in the construction described in Patent Reference 4, because absorbent material is placed near the urethral meatus, urine remains within the absorbent material even if urine is suctioned from within the urethral chamber and it becomes unsanitary.

Furthermore, because the urethral meatus must be positioned accurately to the opening in order to collect urine within the urethral chamber, attaching the urine receiver is troublesome.

The object of the present invention is to provide a urine receiver which is sanitary, easy to attach, and furthermore, prevents urine leakage even when wearer changes positions repeatedly.

More specifically, the present invention provides the following:

(1) A urine receiver, used for suctioning urine discharged by a wearer via a urethral tube for directing urine from the urine receiver into the urine tank by a urine collection processing system, comprising: at least; a liquid-permeable, air-impermeable sheet which is placed opposite of and covering the urethral meatus of the wearer; a leak-proof part which is placed on the surface of this air-impermeable sheet opposite to the urethral meatus and bonds to the outer border of the air-impermeable sheet; an suction part which is provided between the air-impermeable sheet and the leak-proof part and to which the urethral tube is connected; and a sealing means for sealing the space between the air-impermeable sheet and the wearer's skin surface which is provided on the outer border part of the air-impermeable sheet on the urethral meatus side.

The air-impermeable sheet is a sheet having features which enable liquid to pass but does not easily pass air. Through this, urine is passed, and at the same time, the smell of this urine can be prevented from spreading outside of the urine receiver.

The leak-proof part is, for example, a sheet having features which prevent liquid, in this case urine, from passing.

According to the invention in (1), because the air-impermeable sheet is placed opposite of and covering the urethral meatus of the wearer, urine can be received by the entire air-impermeable sheet. Therefore, it is unnecessary to worry about the relative positioning of the urine receiver and the urethral meatus, and the urine receiver can be attached easily.

In addition, a suction part to which a urethral tube is connected is provided between the air-impermeable sheet and the leak-proof part. Through this, if negative pressure is applied to this suction part via a urethral tube in a state wherein the urine discharged from the wearer has reached the air-impermeable sheet, negative pressure is evenly applied within the suction part. As a result, urine is suctioned from the entire surface of the air-impermeable sheet towards the suction part and is suctioned out via the urethral tube. Therefore, because received urine does not remain in one area of the air-impermeable sheet even when the wearer repeatedly changes position, urine leakage from the urine receiver can be prevented.

In addition, because urine is not absorbed by an absorbent material in this construction, urine does not remain within the urine receiver since urine in the suction part is suctioned out, and therefore, this invention is sanitary.

(2) The urine receiver according to (1) wherein the sealing means is formed by a barrier-cuff which can rise up against the air-impermeable sheet.

(3) The urine receiver according to (1) or (2) wherein the sealing means comprises an adhesive layer on the free end sides which can be affixed to the skin of the wearer.

According to the invention in (3), because adhesive layer is provided on free end sides of the sealing means, the free end sides of the sealing means adheres to the skin of the wearer and urine leaking can be prevented without fail.

(4) The urine receiver according to any one of (1) to (3) wherein the sealing means comprises a first gathers which is elastic and expands along the length-direction of the suction part, and this first gathers rises up against the suction part by expanding and contracting.

(5) The urine receiver according to (4) wherein the sealing means comprises a second gathers which is elastic and expands along the width-direction of the suction part.

(6) The urine receiver according to any of (1) to (5) wherein the sealing means can rise up in an inverted funnel-shape towards the wearer.

(7) The urine receiver according to any of (1) to (6) comprising: a liquid-permeable surface material part provided on the surface on the urethral meatus side of the air-impermeable sheet; and a back sheet part which covers the side of the leak-proof part opposite of the air-impermeable sheet.

According to the invention in (7), because a liquid-permeable surface material part is provided on the surface on the urethral meatus side of the air-impermeable sheet, even if urine is discharged from the urethral meatus rapidly and in large amounts, this urine can be temporarily received in the surface material part, and therefore, the overflowing of urine from the urine receiver can be prevented.

Furthermore, because the side of the leak-proof part opposite of the air-impermeable sheet is covered by the back sheet part, leaking of urine from the urine receiver can be prevented with more certainty.

(8) The urine receiver according to any of (1) to (7) comprising at least one pair of electrodes placed on the surface of the urethral meatus side of the air-impermeable sheet, wherein urine can be detected by these electrodes becoming electrically conductive.

According to the invention in (8), urine is detected by placing at least one pair of electrodes on the surface of the urethral side of the air-impermeable sheet and enabling these electrodes to become electrically conductive. Therefore, because urine can be detected by using a simple structure, costs can be reduced.

(9) The urine receiver according to any of (1) to (8) wherein the leak-proof part is cup-shaped.

According to the invention in (9), because the leak-proof part is cup-shaped, the urethral meatus of the wearer can be covered without fail by the leak-proof part. Therefore, urine can be received with more certainty by the air-impermeable sheet of the urine receiver and the frequency of urine leakage can be reduced.

(10) A urine collection processing system for suctioning urine discharged from a wearer into a urine tank via an urethral tube comprising: a urine receiver according to any one of (1) to (9); a urine tank which is connected to this urine receiver via a urethral tube; and a vacuum pump which sucks out urine received by the urine receiver by suctioning the air within the urine tank and collecting urine within the urine tank.

According to the urine receiver and the urine collection processing system implementing this urine receiver of the present invention, the following effects can be attained. Because the air-impermeable sheet is placed opposite of and covering the urethral meatus of the wearer, urine can be received by the entire air-impermeable sheet. Therefore, it is unnecessary to worry about the relative positioning of the urine receiver and the urethral meatus, and the urine receiver can be attached easily.

In addition, a suction part to which a urethral tube is connected is provided between the air-impermeable sheet and the leak-proof part. Through this, if negative pressure is applied to this suction part via a urethral tube in a state wherein the urine discharged from the wearer has reached the air-impermeable sheet, negative pressure is evenly applied within the suction part. As a result, urine is suctioned from the entire surface of the air-impermeable sheet towards the suction part and is suctioned out via the urethral tube. Therefore, because received urine does not remain in one area of the air-impermeable sheet even when the wearer repeatedly changes position, urine leakage from the urine receiver can be prevented.

In addition, because urine is not absorbed by an absorbent material in this construction, urine does not remain within the urine receiver since urine in the suction part is suctioned out, and therefore, this invention is sanitary.

DESCRIPTION OF THE PREFERRED EMBODIMENT

Embodiments of present invention are described below based on the drawings. In the description of the embodiments below, the same reference numbers are affixed to the same construction requisite and explanations therefor are omitted or simplified.

[First Embodiment]

Figure 1:
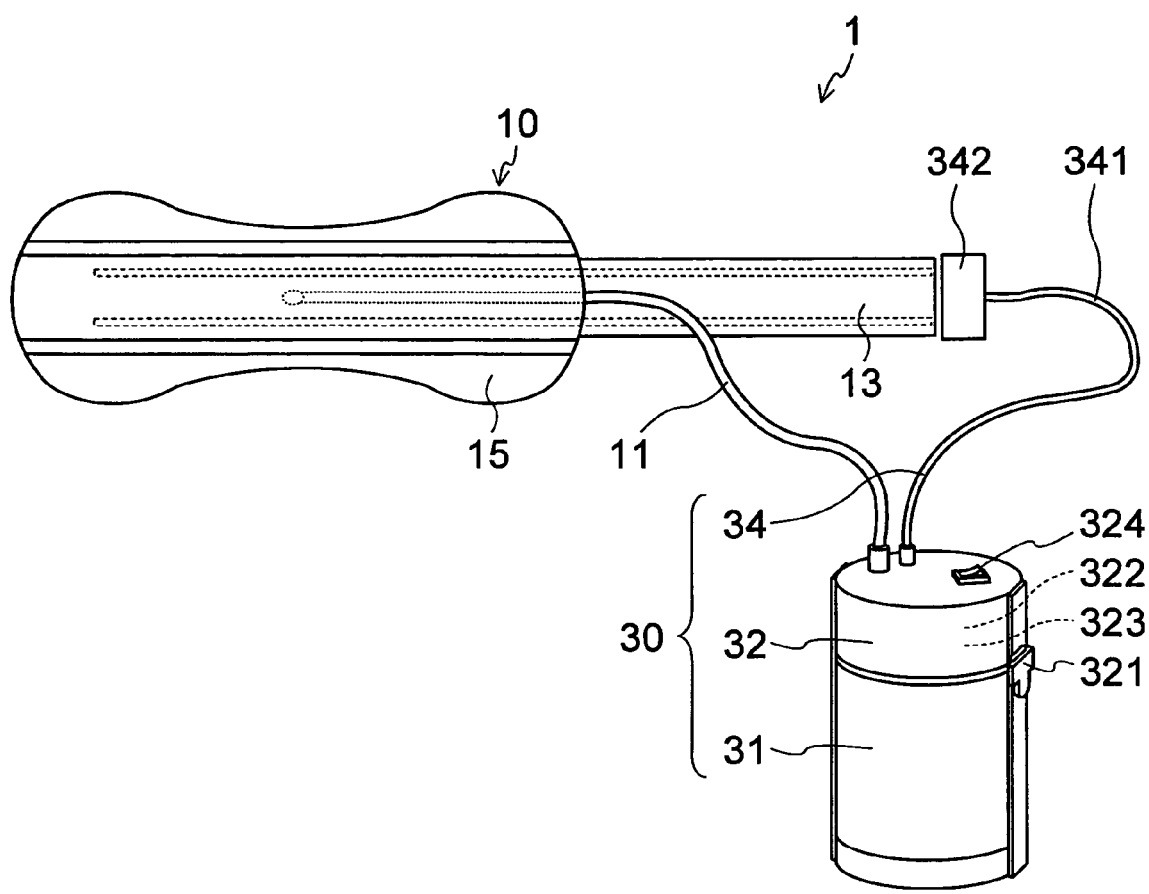
FIG. 1 is a perspective view showing a urine collection processing device to which a urine receiver according to a first embodiment of the present invention is applied.

A perspective pattern view of a urine collection processing device to which a urine receiver according to a first embodiment of the present invention is applied is shown in FIG. 1.

Urine collection processing device 1 is a device for processing urine discharged by a wearer comprising: a urine receiver 10 for receiving discharged urine; and a main urine collection processing device 30 which is connected to the urine receiver 10 via a urethral tube 11.

The main urine collection processing device body 30 comprises: a main urine tank body 31 which is connected to the urethral tube 11; a lid part 32 which is provided on the main urine tank body 31 and can be opened and closed; and a urine detection mechanism 34 which extends from the lid part 32 and is connected to the urine receiver 10.

An un-illustrated water tank which can be removed by opening the lid part 32 is stored within the main urine tank body 31.

The urine detection mechanism 34 detects urine in the urine receiver 10. This urine detection mechanism 34 comprises: wiring 341 which extends from the main urine collection processing device body 30; and clips 342 which are provided at the end of these two cables. Clips 342 hold electrodes 131 of the urine receiver 10, described hereafter.

The lid part 32 is locked onto the main urine tank body 31 by a lock mechanism 321 and hermetically seals the urine tank. This lid part 32 comprises: a vacuum pump 322 which is connected to the urine tank; and a controller 323 which drives the vacuum pump 322 according to detection signals from the urine detection mechanism.

The vacuum pump 322 suctions out urine received by the urine receiver 10 via the urethral tube 11 by suctioning air within the main urine tank body 31 and collects urine in the main urine tank body 31.

A control circuit, timer circuit and battery are embedded in the controller 323. The controller 323 starts the timer of the timer circuit and activates the vacuum pump 322 when detection signals are received from the urine detection mechanism 34. In the present embodiment, the vacuum pump 322 is activated according to the detection signals from the urine detection mechanism 34. However, it is not limited thereto, and furthermore, the timer can be started regularly for the purpose of ventilation and can be started by detecting excessive humidity by a humidity sensor. The electrical current applied to the urine detection mechanism 34 is preferably 0.01 to 0.1 mA at an applied voltage of 6 to 12V, so as not to affect the body.

The vacuum pump 322 and controller 323, above, are turned on and off by a manual switch 324 provided on the upper surface of the lid part 32. Through this, cleaning and maintenance of the urine collection processing device 1 is possible.

The urine receiver 10 is formed from flexible material, is attached between the thighs of the wearer, and receives urine discharged from the urination part of the wearer.

Figure 2:
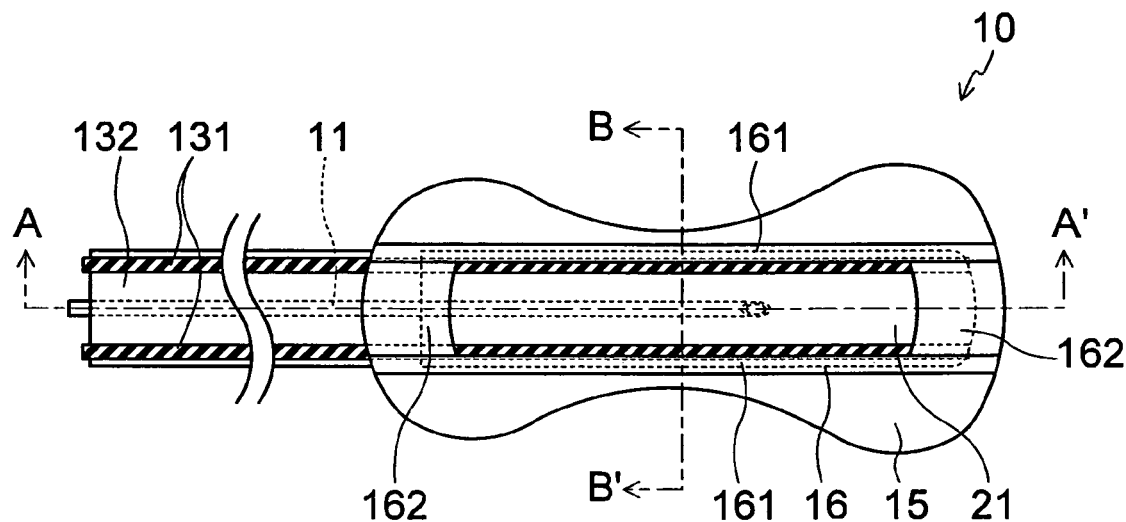
FIG. 2 is a top view of the urine receiver according to the embodiment.
Figure 3:
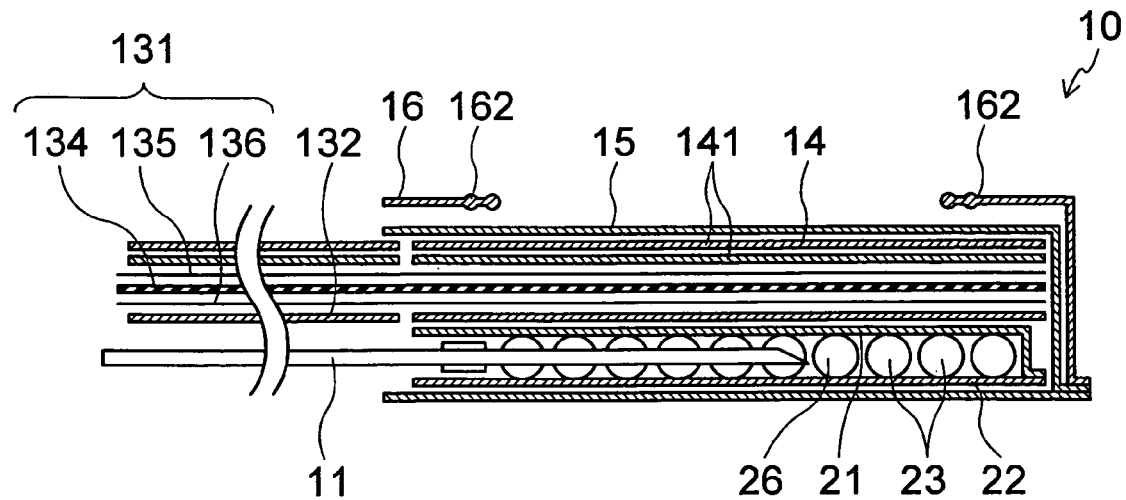
FIG. 3 is a cross-sectional pattern view cut in the direction of A to A' in FIG. 2.
Figure 4:
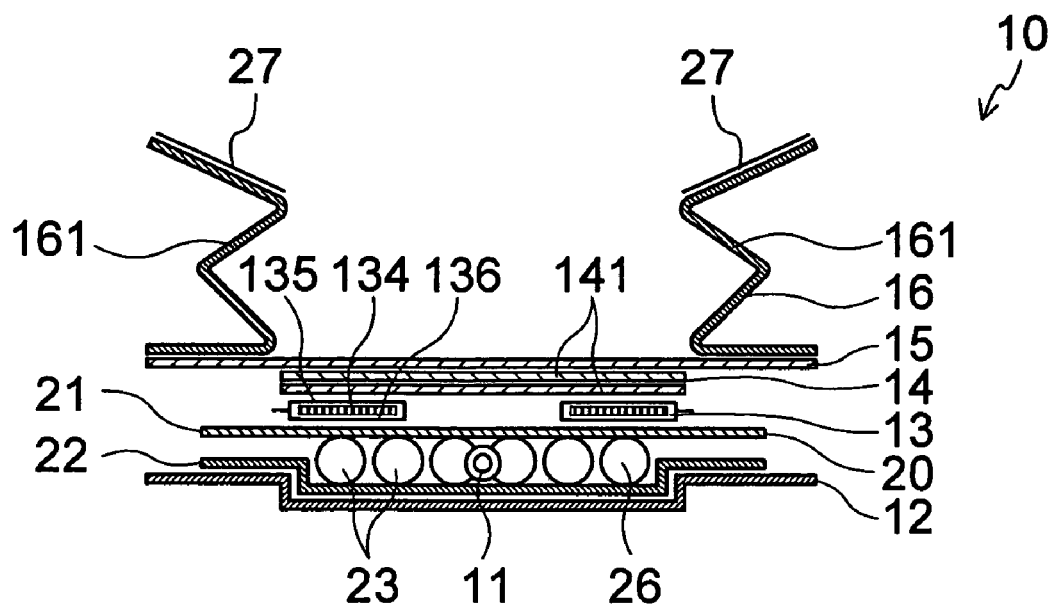
FIG. 4 is a cross-sectional pattern view cut in the direction of B to B' in FIG. 2.

FIG. 2 is a top view of the urine receiver according to the embodiment; FIG. 3 is a cross-sectional pattern view cut in the direction of A to A' in FIG. 2; and FIG. 4 is a cross-sectional pattern view cut in the direction of B to B' in FIG. 2;

This urine receiver 10 is board-shaped and formed from a back sheet part 12, a main urine receiver body 20, a urine detection sensor part 13, a surface material part 14, a surface sheet part 15, and a gathers part 16, layered in order from the bottom. Although the foregoing components 20 and 12 to 16 are shown separately in FIG. 3 and FIG. 4, it is in reality a unit.

Figure 5:
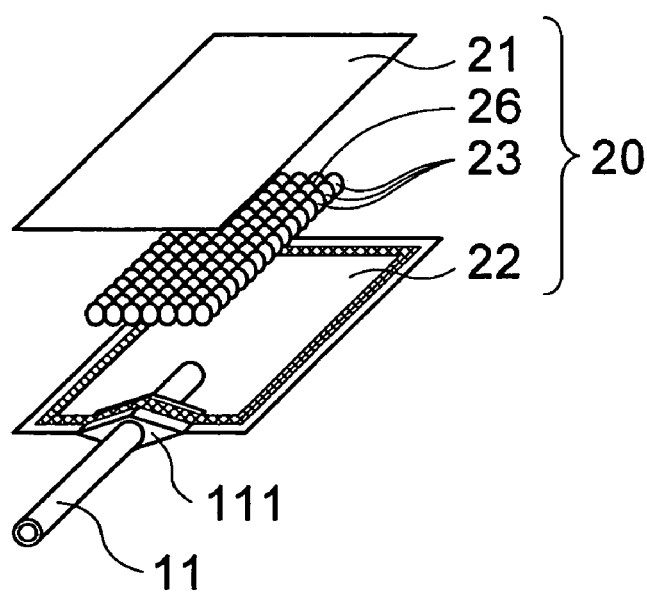
FIG. 5 is an analytical perspective view of the main body of the urine receiver according to the embodiment.

FIG. 5 is an analytical perspective view of the main urine receiver body 20.

The main urine receiver body 20 has a roughly rectangular board-shape and comprises: a liquid-permeable, air-impermeable sheet 21; a leak-proof part 22 which is placed on the surface of this air-impermeable sheet 21 opposite of the urethral meatus of the wearer; and a suction part 26 which is provided between the air-impermeable sheet 21 and the leak-proof part 22.

The permeability of the air-impermeable sheet 21 measured according to the permeability A method prescribed in 6.27.1 of JIS L 1096 is within the range of 0 to 100 cc/cm$^2$/sec, and preferably 0 to 50 cc/cm$^2$/sec, in a moistened state.

Here, a moistened state indicates a state wherein the moisture content calculated from the equation below is over 100%:

Moisture content=(sheet weight when moistened−sheet weight when dry)/(sheet weight when dry)

In addition, the above-mentioned permeability is within the range of 20 to 200 cc/cm$^2$/sec, and preferably 20 to 50 cc/cm$^2$/sec, in a dry state.

Here, a dry state indicates a state of being left sitting for a sufficient amount of time in an atmosphere of 20° C. and RH60%.

The suction part 26 is a hermetically-sealed space formed between the air-impermeable sheet 21 and leak-proof part 22 wherein a plurality of space retention materials 23 are stored. More specifically, they are aligned in one row, in a non-fixed state, between the air-impermeable sheet 21 and the leak-proof part 22.

The urethral tube 11 is connected to one side of the suction part 26 of the main urine receiver body 20 in a length-direction. More specifically, the outer border of the air-impermeable sheet 21 and the outer border of the leak-proof part 22 are bonded together with the urethral tube 11 sandwiched between. Through this, a hermetically-sealed space is formed by the air-impermeable sheet 21 and the leak-proof part 22, and at the same time, the urethral tube 11 is in communication with this hermetically-sealed space.

A hermetic-sealing joint 111 is attached on to the section of the urethral tube 11 which is sandwiched between the air-impermeable sheet 21 and the leak-proof part. This prevents the urethral tube 11 from becoming crushed and also facilitates the bonding of the air-impermeable sheet 21 and the leak-proof part 22.

Figure 6:
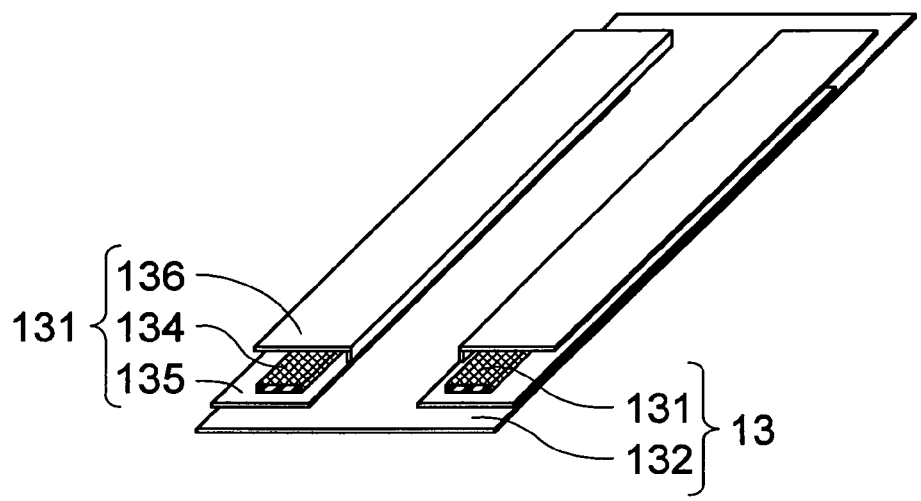
FIG. 6 is a perspective view of a pair of electrodes according to the embodiment and a cross-sectional view of the conductors comprising these electrodes.
Figure 6:

FIG. 6(a) is a perspective view of a urine detection sensor part 13.

The urine detection sensor part 13 comprises: a pair of electrodes 131 which are placed roughly parallel; and a band-shaped electrode sheet 132 which envelopes these electrodes 131 and are connected to the side of the main urine receiver body 20 in the length-direction. Each electrode 131 is coated with permeable coating material 135 and 136 which coat the conductors 134 and the front and back surfaces thereof.

FIG. 6(b) is a cross-sectional view of the conductors 134 comprising the electrodes 131.

Insulator film is attached to the back surface of the conductors 134.

One end of a pair of electrodes 131 extends along both side-borders of the air-impermeable sheet 21 of the main urine receiver body 20 in parallel with each other. Because this pair of electrodes 131 are placed apart, if urine collects between these electrodes 131, urine can be detected though electrical continuity. The other end of this pair of electrodes 131 is exposed from the end of an electrode sheet 132 and is connected to clips 342 of a urine detection mechanism 34.

Although one pair of electrodes 131 is provided in the present embodiment, it is not limited thereto, and three electrodes or more can be provided in order to enhance the sensitivity of the urine detection sensor part 13.

Figure 7:
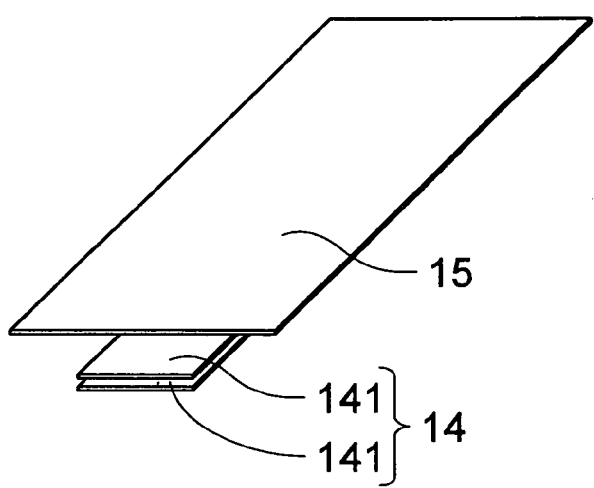
FIG. 7 is a perspective view of a surface material part according to the embodiment.

FIG. 7 is a perspective view of the surface material part and surface sheet part 15.

Surface material part 14 is provided on the urethral meatus side of the air-impermeable sheet 21, formed by layering two liquid-permeable cushion sheets 141, and temporarily receives urine discharged by the wearer. Therefore, it is preferable that the width of the cushion sheet 141 is almost the same as the width of the air-impermeable sheet 21.

The surface sheet part 15 covers the air-impermeable sheet 21 surface of the main urine receiver body 20. Back sheet part 12 covers the side of the leak-proof part 22 of the main urine receiver body 20 opposite of the air-impermeable sheet in order to prevent urine from leaking. These surface sheet part 15 and back sheet part 12 have an hourglass-shape and are connected together on the outer border of the main urine receiver body 20.

Gathers part 16, as a sealing means, is formed from a barrier-cuff which can rise up against the air-impermeable sheet 21, provided along the entire circumference of the outer border part of the air-impermeable sheet 21 of the main urine receiver body 20, and seals the space between the main urine receiver body 20 and the skin surface of the wearer.

The gathers part 16 comprises: side gathers 161 as a pair of first gathers which expands along the main urine receiver body 20 in a length-direction; and round gathers 162 as a pair of second gathers which expands along the main urine receiver body 20 in a width-direction.

These gathers 161 and 162 can rise up against the main urine receiver body 20 by expanding and contracting.

Adhesive layer 27 which can be attached to the wearer's skin is formed on the free end sides (end side) of the gathers 161 and 162. This adhesive layer 27 can be formed from any water-resistant, pressure-sensitive adhesive which is medically-approved, such as hydrocolloid layer and hydro gel adhesive. As adhesive which can be attached and removed with comparatively no pain, and at the same time, has adhesive characteristics enabling attachment to the delicate skin of the wearer, that which is formed from cross-linked polymer to which plasticizer is added and forms a three-dimensional matrix is ideal.

The gathers part 16 prevents urine which trickles down the wearer's skin from leaking. In particular, this is effective when urine is discharged rapidly in large amounts because all of the urine cannot be received by the surface sheet part 15. Although one pair of round gathers 162 is provided in the present embodiment, it is not limited thereto and a round gathers provided only on the back side is also possible. The reason for this is because in elderly-care, most patients do not lay face-down.

Figure 8:
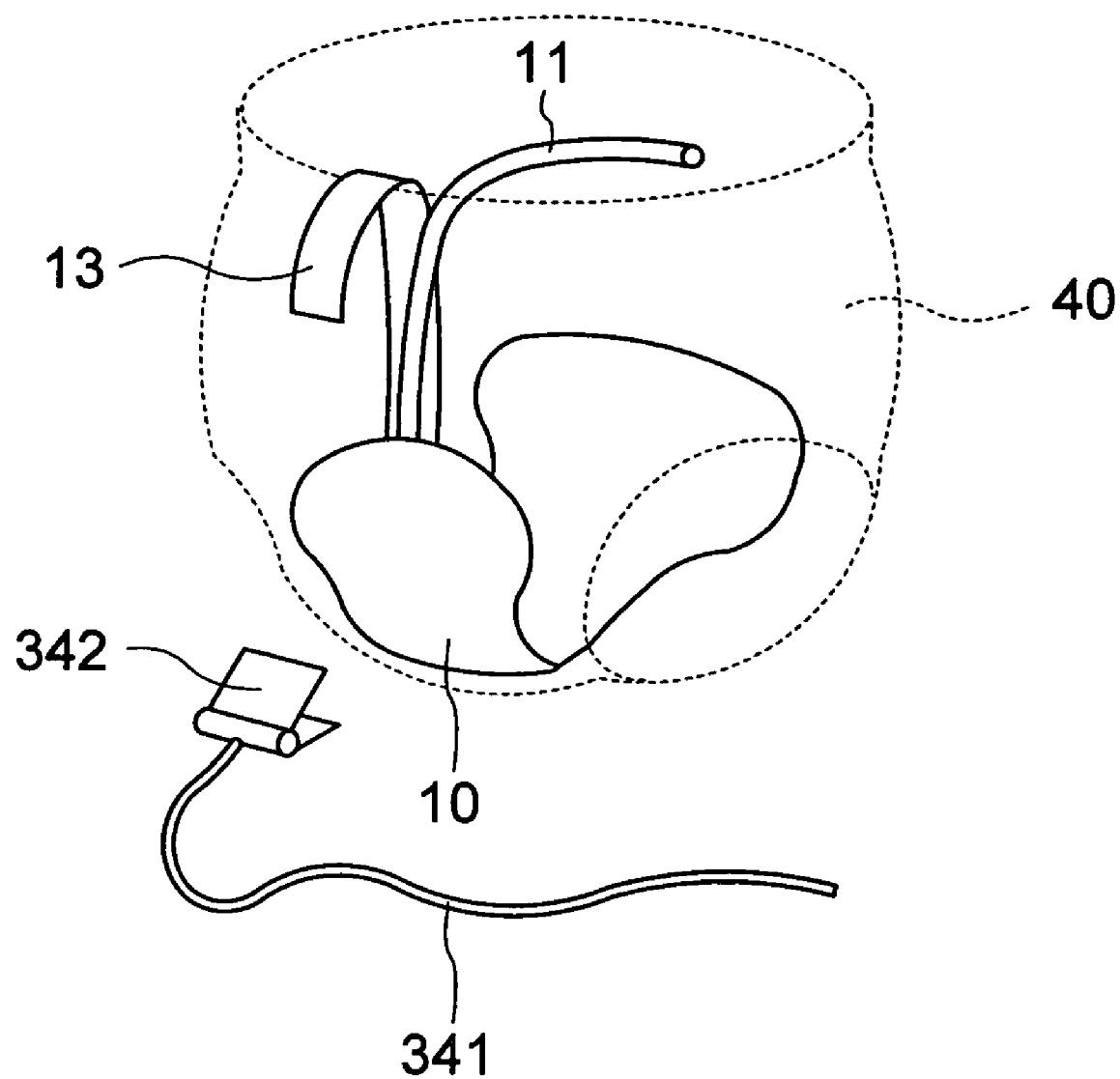
FIG. 8 is a perspective view of a cover pants to which a urine receiver according to the embodiment is applied.

FIG. 8 is a perspective view of cover pants 40 to which the urine receiver 10 described above is applied.

The cover pants 40 are pant wherein a urine receiver 10 is embedded. The urine receiver 10 is placed in the section between the legs of the cover pants 40, with the air-impermeable sheet 21 facing inward. At this time, because the urine receiver 10 is slightly rolled up in a length-direction to the crotch of the wearer, gathers 161 and 162 expand and contract inward and rises up in an inverted funnel-shape (drawing omitted). Therefore, when a wearer wears these cover pants 40, the air-impermeable sheet 21 of the urine receiver 10 is placed opposite of and covering the urethral meatus of the wearer, and at the same time, the urethral tube 11 and the urine detection sensor part 13 are exposed from the front of the body.

Although the urine receiver 10 is attached to the cover pants 40 in the present embodiment, it is not necessarily limited thereto and can be attached to diapers with tape fasteners, pants-type diapers, or textile diapers, such as conventional diaper pads, incontinence pads, and sanitary napkins.

Figure 9:
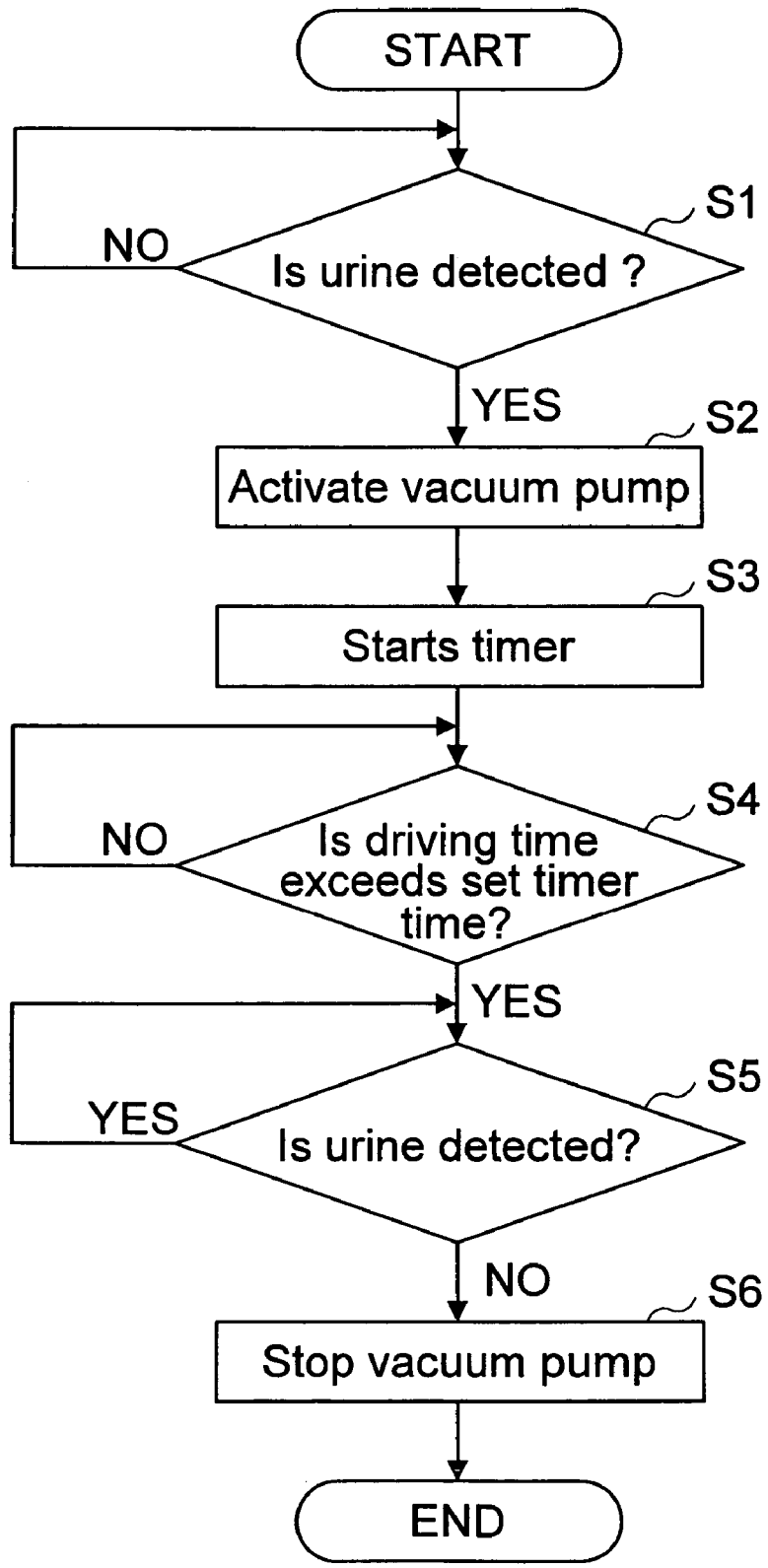
FIG. 9 is a flowchart of the urine collection processing device according to the embodiment.

The foregoing urine collection processing device 1 operates as follows:

FIG. 9 is a flowchart of the urine collection processing device 1.

When urine is discharged into the urine receiver 10, the pair of electrodes 131 of the urine detection sensor part 13 are soaked in urine, becomes electrically conductive, and urine is detected (S1). Controller 323 receives the detection signal via urine detection mechanism 34. Then, the controller 323 activates vacuum pump 322 and starts the timer (S2 and S3). This timer is, for example, set to two to three minutes, and the controller 323 drives the vacuum pump 322 during the time to which this timer is set.

If the driving time of the vacuum pump 322 exceeds the set timer time (S4) and detection signals are received (S5), the controller 323 continues to drive the vacuum pump 322.

On the other hand, if the driving time of the vacuum pump 322 exceeds the set timer time (S4) and detection signals are not received (S5), the controller 323 stops the vacuum pump 322.

In addition, the vacuum pump 322 suctions urine from the main urine receiver body 20 with the following mechanism:

Urine discharged from the wearer is temporarily received in the cushion sheet 141 of the surface material part 14 and subsequently reaches the air-impermeable sheet 21.

If the vacuum pump 322 is driven in this state, negative pressure is applied to the suction part 26 between the air-impermeable sheet 21 and the leak-proof part 22 due to suction power from the vacuum pump. At this time, because space retention material 23 is positioned so that this suction part 26 is not crushed, the vacuum pressure from the vacuum pump 322 is evenly applied within the suction part 26. As a result, urine is suctioned from the entire front surface of the air-impermeable sheet 21 to the main urine receiver body 20 and is suctioned out via the urethral tube 11.

According to the present embodiment, the following effects can be attained.

Because the air-impermeable sheet 21 is placed opposite of and covering the urethral meatus of the wearer, urine can be received by the entire surface of the air-impermeable sheet. Therefore, it is unnecessary to worry about the relative positioning of the urine receiver and the urethral meatus, and the urine receiver can be attached easily.

A suction part 26 is provided between the air-impermeable sheet 21 and the leak-proof part 22. Through this, urine is suctioned from the entire front surface of the air-impermeable sheet 21 towards the suction part 26 and suctioned out via the urethral tube 11. Therefore, because received urine does not remain in one area of the air-impermeable sheet even when the wearer repeatedly changes position, urine leakage from the urine receiver can be prevented.

In addition, the urine receiver 10 and vacuum pump 322 can be miniaturized. Through this, the burden of excretion care for wearers placed upon care-givers can be lightened. Furthermore, not only can the amount of waste be reduced, conventional work involving placing a pad underneath the buttocks of the wearer can be minimized.

Because urine can be suctioned out repeatedly by the urine receiver 10, the frequency of replacing pads can be reduced. Furthermore, because it is not necessary to manufacture individual products according to urine absorbency amount, such as with diaper pads, manufacturing costs can be reduced.

Because this invention is not constructed such that urine is not absorbed by absorbent material, urine does not remain within the urine receiver 10 due to the suction of the urine within the suction part 26, skin and genitals are not left damp for a long period of time or dampened repeatedly, and therefore, it is sanitary. As a result, rashes and skin irritation can be contained.

Because a liquid-permeable surface material part 14 is provided on the urethral meatus side of the air-impermeable sheet 21, even if urine is discharged rapidly in large amounts from the urethral meatus, this urine can be temporarily received by the surface material part 14, and therefore, the overflowing of urine from the urine receiver 10 can be prevented.

Because the surface of the leak-proof part 22 opposite of the air-impermeable sheet 21 is covered with back sheet 12, the overflowing of urine from the urine receiver 10 can be prevented with further certainty.

Urine is detected by providing at least one pair of electrodes 131 on the urethral meatus side of the air-impermeable sheet 21 and enabling these electrodes 131 to become electrically conductive. Therefore, urine can be detected using a simple structure and costs can be reduced.

Because urine receiver 10 is formed from flexible material, special supporters such as those conventionally used are not implemented, and the urine receiver can be attached easily to diapers with tape fasteners, pants-type diapers, and textile diapers, for example.

More specifically, the foregoing urine collection processing device is constructed as follows:

1. Main Urine Collection Processing Device Body
Urine tank: capacity of approximately 750 cc 2. Urethral Tube
Silicone tube (inner diameter of ø4 mm, outer diameter of ø6 mm, and length of 1500 mm)

3. Urine Receiver 3-1 Back Sheet Part
A three layer-construction comprising a bottom layer, middle layer, and a top layer, wherein layers are simply joined by spiral HMA
Bottom layer: PP spun bond N.W. 15 g/m$^2$
Middle layer: polyethylene film with a thickness of 15 µm
Top Layer: SMS N.W. 35 g/m$^2$ 3-2 Main Urine Receiver Body
Air-impermeable sheet: SMS nonwoven fabric (54 g/m$^2$)
Space retention material: styrofoam beads (diameter of approximately 6 mm)
Leak-proof part: PET/PE (12 µm/40 µm) laminated film with PE placed on the air-impermeable sheet side
Hermetic-sealing joint: molded PE part
The outer borders of the air-impermeable sheet and the leak-proof part are adhered by 2 mm heat-sealing 3-3 Urine Detection Sensor Part
Coating material: thermal bond nonwoven fabric (25 g/m$^2$ and a density of 0.01 g/cm$^3$)
Conductor: aluminum foil (width of 10 mm)
Insulator film: PE film (width of 10 mm)

3-4 Surface Material Part
Cushion sheet: thermal bond nonwoven fabric (25 g/m$^2$)×2

3-5 Surface Sheet
thermal bond nonwoven fabric (25 g/m$^2$)

3-6 Gathers Part
Side gathers and round gathers: almost the same as gathers for sanitary napkins

[Second Embodiment]

Figure 10:
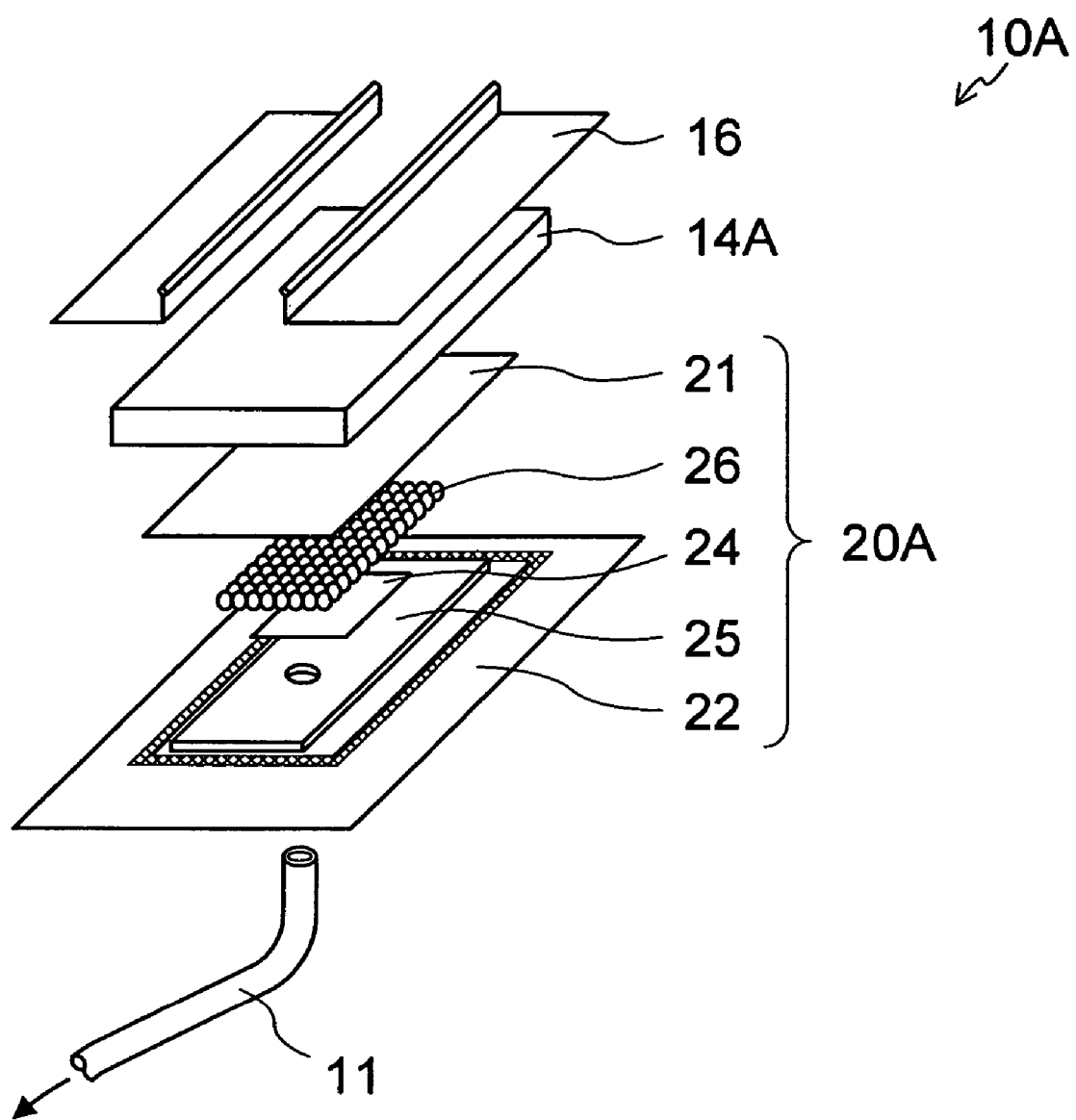
FIG. 10 is an exploded perspective view of the urine receiver according to a second embodiment of the present invention.

FIG. 10 is a perspective view of a urine receiver 10A according to a second embodiment of the present invention.

This embodiment differs from the first embodiment in that the surface sheet in the first embodiment is not provided, the surface material part 14A construction differs, and the main urine receiver body 20A construction differs.

Specifically, a liquid-passing sheet 24 and a support sheet 25 are layered between the space retention material 23 and leak-proof part 22. The liquid-passing sheet 24 is joined to the support sheet over its entire surface, and the support sheet 25 is joined to the leak-proof part 22 over its entire surface.

An insertion hole is provided in the leak-proof part 22 and the support sheet for inserting the urethral tube 11.

In particular, the foregoing urine collection processing device has a construction which differs from the first embodiment in the following ways:

Leak-proof part: PE film with a thickness of 15 μm
Support sheet: PE foam sheet with a thickness of 2 mm
Liquid-passing sheet: nylon flatwoven mesh sheet (gauge: approximately 0.04 mm; number of threads implanted: 100/cm)
Surface material part: thermal bond nonwoven fabric (225 g/m$^2$, thickness of 20 m, and density of 0.01 g/cm$^3$)

[Third Embodiment]

The present embodiment differs from the second embodiment in that a surface sheet is provided and the surface material part differs.

More specifically, in order to enhance temporary collection of liquid, the surface material part comprises two layered cushion sheets.

In particular, the foregoing urine collection processing device has a construction which differs from the second embodiment in the following ways:
Surface sheet: thermal bond nonwoven fabric (25 g/m$^2$ and density of 0.01 g/cm$^3$)
Cushion sheet: thermal bond nonwoven fabric (25 g/m$^2$)

[Fourth Embodiment]

Figure 11:
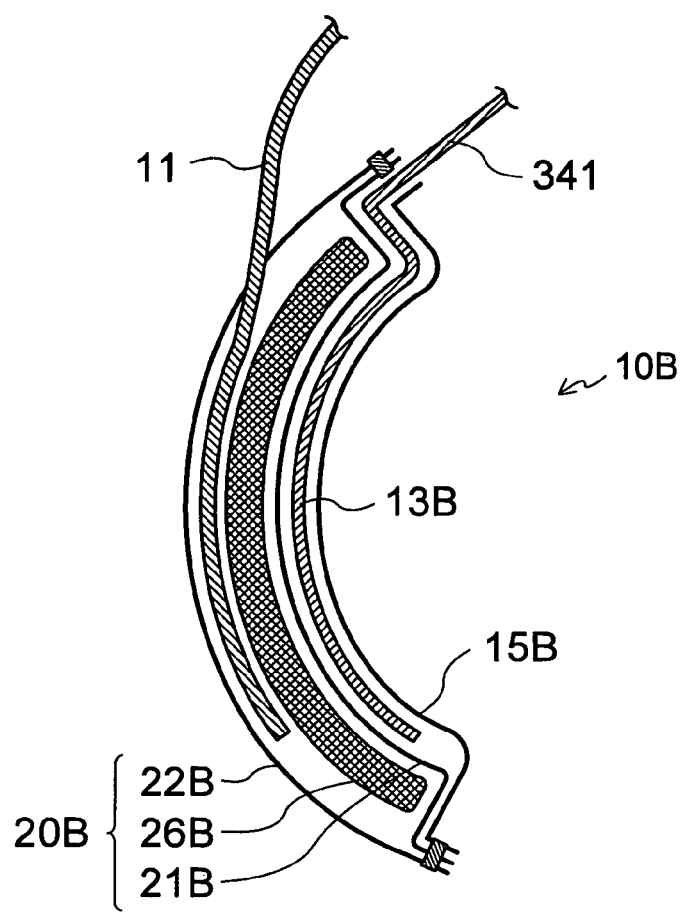
FIG. 11 is a vertical-sectional view of the urine receiver according to a fourth embodiment of the present invention.
Figure 12:
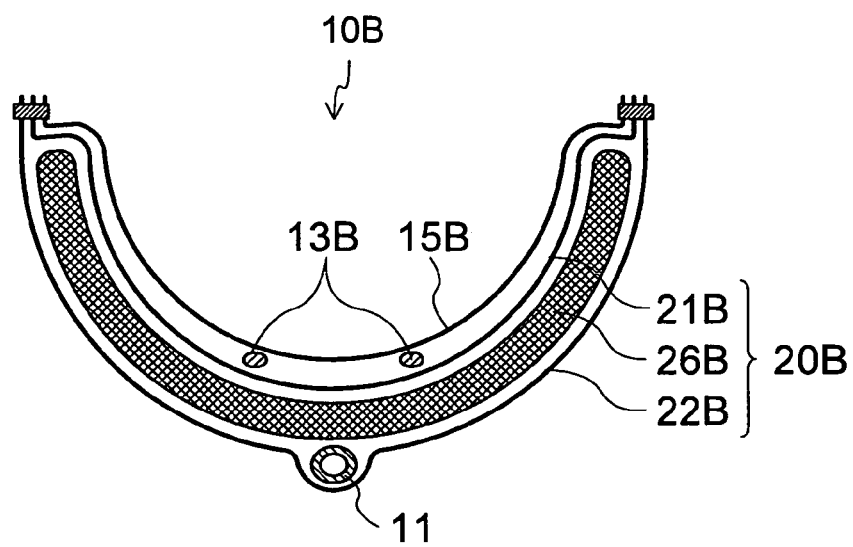
FIG. 12 is a horizontal-sectional view of the urine receiver according to the embodiment.
Figure 13:
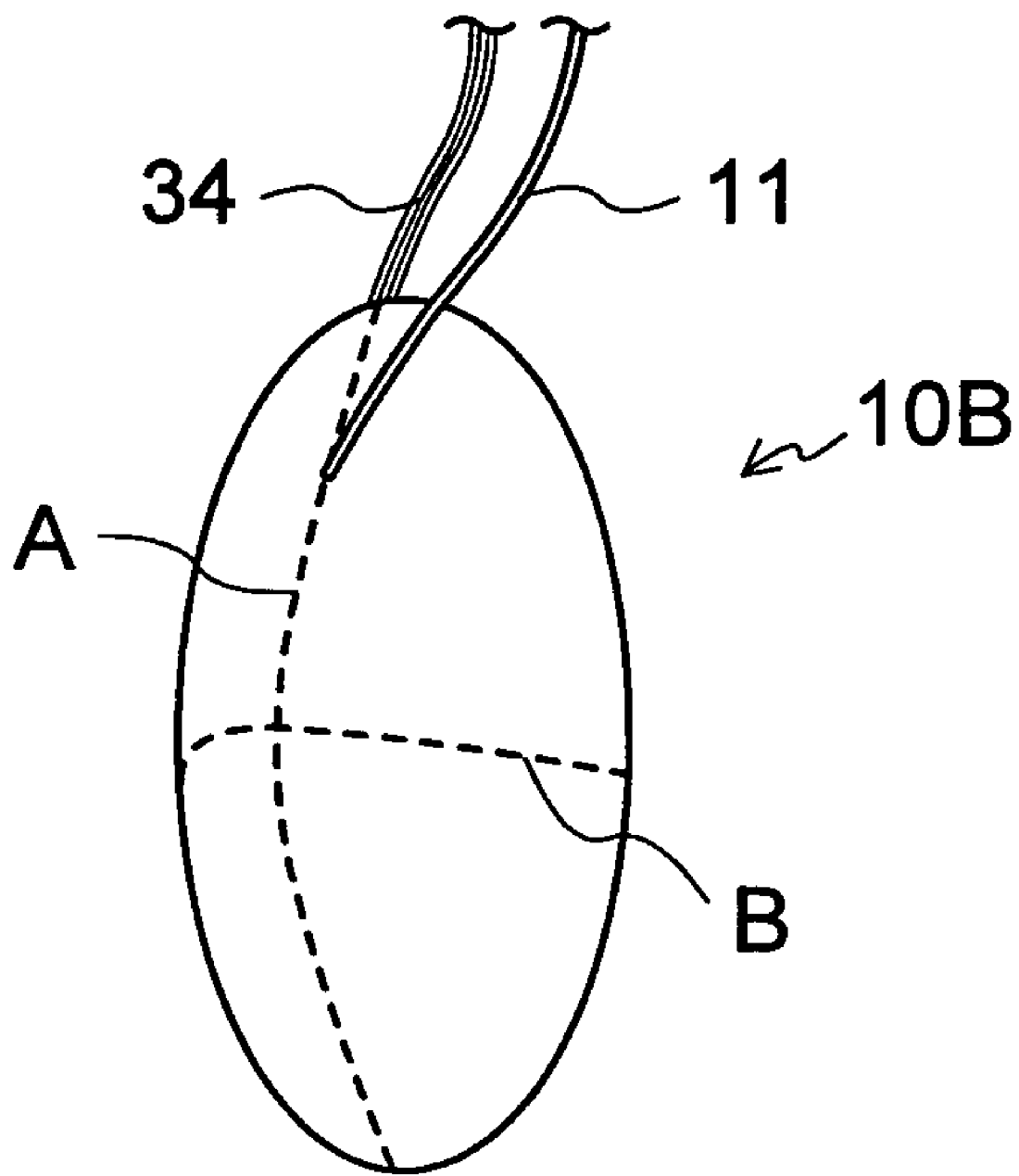
FIG. 13 is a perspective view of the urine receiver according to the embodiment.
Figure 14:
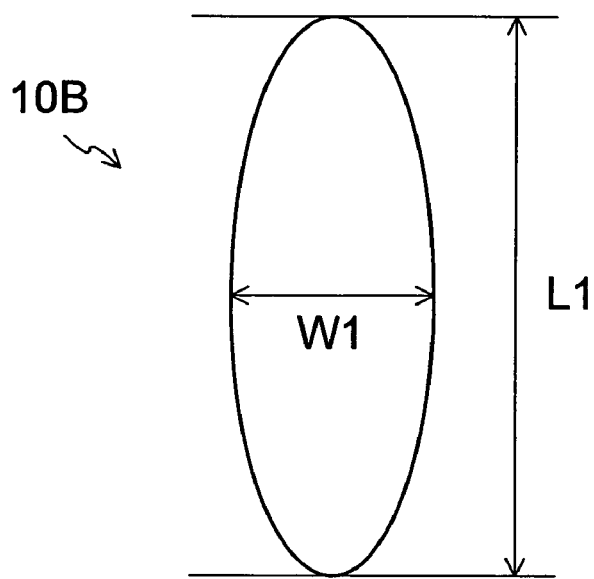
FIG. 14 is a top pattern view of the urine receiver according to the embodiment.

FIG. 11 is a vertical-sectional view of a urine receiver 10B according to a fourth embodiment of the present invention; FIG. 12 is a horizontal-sectional view of the urine receiver 10B; FIG. 13 is a perspective view of the urine receiver 10B; and FIG. 14 is a top pattern view of the urine receiver 10B.

The present embodiment differs from the first embodiment in that the shape and construction of the urine receiver 10B differs.

Figure 15:
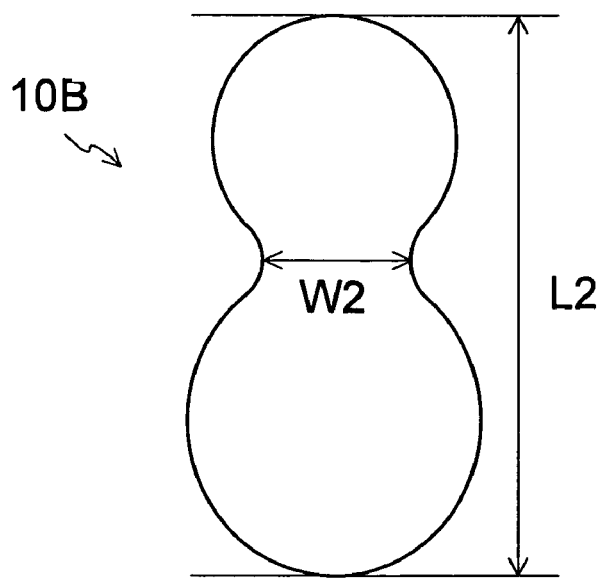
FIG. 15 is a top pattern view showing an example of a variation of the urine receiver according to the embodiment.

In otherwords, the urine receiver 10B is cup-shaped. More specifically, center line A which extends in the length-direction of the urine receiver 10B curves to the shape of the wearer's body and the center section cups outward. In addition, the center section of center line B which extends in the lateral-direction of the urine receiver 10B also cups outward. The measurement of the cupping of the urine receiver 10B is, in particular, preferably 10 to 80 mm. Furthermore, as shown in FIG. 14, the urine receiver 10B is an ellipsoid when viewed from the top, the width measurement W1 of the crotch area is preferably 50 to 80 mm, and the length measurement L1 preferably 200 to 350 mm. It is not limited thereto, however, and as shown in FIG. 15, the urine receiver 10B have an hourglass-shape, the width measurement W2 of the crotch area can be 50 to 80 mm, and the length measurement L2, 200 to 350 mm.

A urethral tube 11 is connected to the urine receiver 10B, as is in the first embodiment, and the urine receiver 10B comprises a main urine receiver body 20B, a urine detection sensor part 13B and a surface sheet part 15B, but does not comprise a back sheet, a surface material part, or a gathers part.

The urethral tube 11 is formed from polyvinyl, silicone, or PE, for example. The inner diameter of the tube is, for example, 1 to 10 mm.

The conductors configuring the urine detection sensor part 13B are formed from conductive materials such as carbon, aluminum, copper, or silver. If carbon powder is used, the conductor is formed, for example, by combining hot-melt resin and carbon powder and bead coating over a nonwoven fabric. In this case, the combination percentage of the hot-melt resin and carbon powder is preferably that wherein carbon is 50% by weight or more.

The surface sheet part 15B is preferably formed from a low-density air through nonwoven fabric with low remaining water content. In particular, a 20 g/ms air through nonwoven fabric with density of 0.88 g/cm$^3$ constructed by 4-denier water-processed PE/PET synthetics is preferable. In addition, the density of this air through nonwoven fabric is preferably 0.005 to 0.01 g/cm$^3$.

The main urine receiver body 20B comprises a air-impermeable sheet 21B, a leak-proof part 22B, and a suction part 26B, as in the first embodiment.

The leak-proof part 22B is formed from polyethylene film, polyethylene foam, closed-cell polyurethane foam, flexible rubber, or plastic, for example. More particularly, the leak-proof part 22B is formed from 50 g/m$^2$ of heat-molded polyethylene foam.

The foregoing urethral tube 11 extends from the upper side of the main urine receiver body 20B along the space retention part 23 and reaches the bottom half of the main urine receiver body 20B.

Suction part 26B is, for example, formed from fibrous frame material. More particularly, it is formed by polyethylene foam beads of 2 to 10 mm in diameter or 8- to 15-denier, 3 to 10 mm dimension air through nonwoven fabric.

Air-impermeable sheet 21B is formed from hydrophilic fibers such as rayon. The permeability of the air-impermeable sheet 21B measured according to the afore-mentioned permeability A method is preferably 20 to 50 cc/cm$^2$/sec in a dry state and 0 to 50 cc/cm$^2$/sec in a moistened state. More particularly, it is formed from 54 g/m$^2$ water-processed SMS nonwoven fabric (spun bond layer . . . 22 g/m$^2$, melt-blown layer . . . 10 g/m$^2$, spun bond layer . . . 22 g/m$^2$).

The present invention is not limited to the foregoing embodiments, and modifications, improvements, and the like within the scope of achieving the object of the present invention are included within the present invention.

Figure 16:
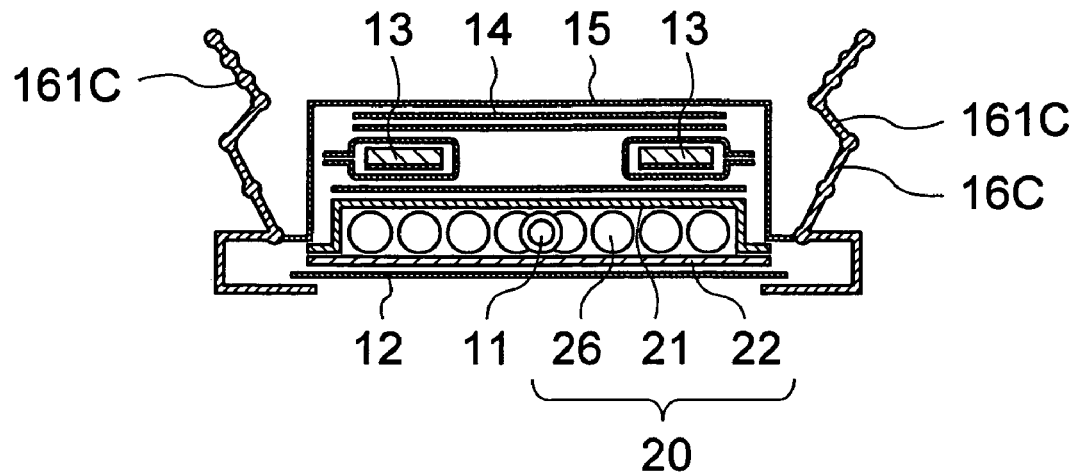
FIG. 16 is a cross-sectional pattern view of the urine receiver according to a variation example of the first embodiment of the present invention.

For example, in the foregoing first embodiment, although gathers part 16 is provided on the outer border of the air-impermeable sheet 15, it is not limited thereto, and as shown in FIG. 16, the gathers 16C can be sandwiched between the outer borders of the air-impermeable sheet 15 and the leak-proof part 22. Through this, the air-impermeable sheet 15 and leak-proof part 22 can be joined without fail.

Figure 17:
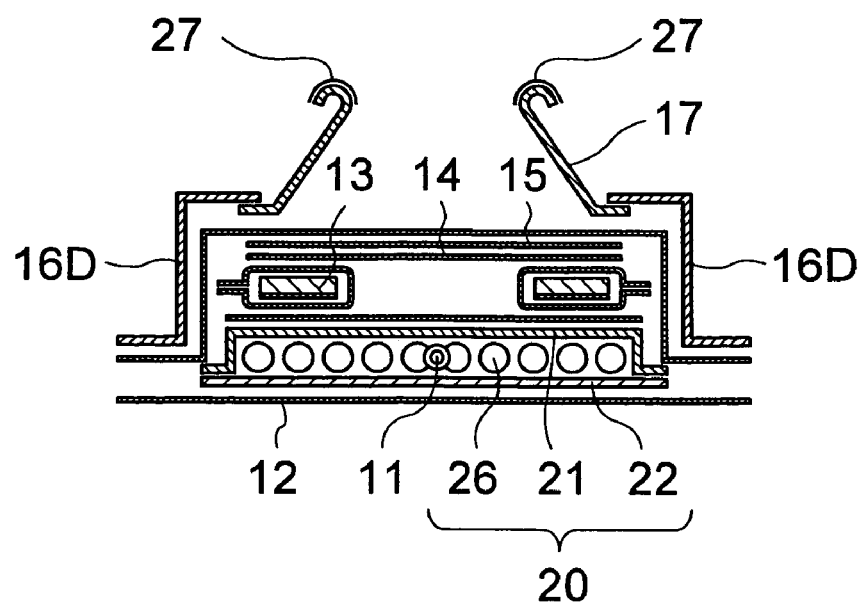
FIG. 17 is a cross-sectional pattern view of the urine receiver according to a variation example of the second embodiment of the present invention.

In addition, as shown in FIG. 17, it is possible for the gathers part 16D to not rise up and a molded inverted funnel-shaped part made out of polyurethane or silicone can be attached.

Figure 18:
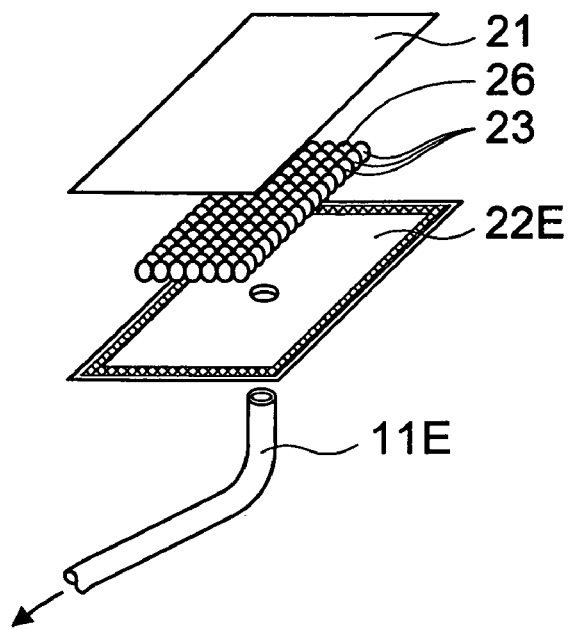
FIG. 18 is a perspective view of the main body of the urine receiver according to a variation example of a third embodiment of the present invention.
Figure 19:
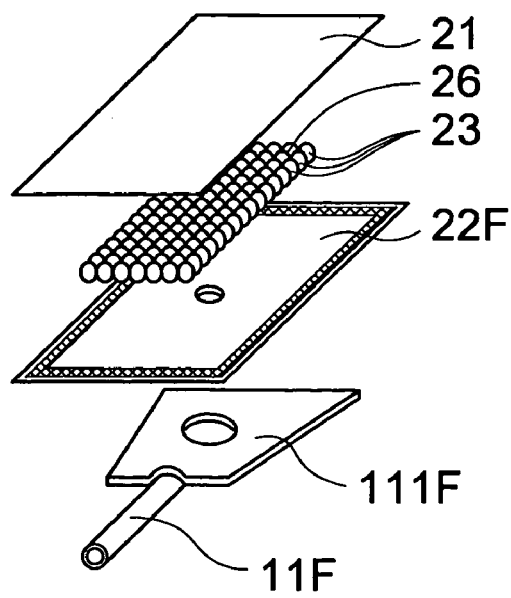
FIG. 19 is a perspective view of the main body of the urine receiver according to a variation example of the fourth embodiment of the present invention.

In addition, in the foregoing first embodiment, although the urethral tube is connected to the main urine receiver body 20 on one side in the length-direction, it is not limited thereto, and a hole can be provided on the bottom surface of a leak-proof part 22 E, and a urethral tube 11E can be inserted into this hole and connected, as shown in FIG. 18. Furthermore, as shown in FIG. 19, a hermetic-sealing joint 111F can be used as a bent pipe, a urethral tube 11F can be connected to the hermetic-sealing joint 111F from one side of the main urine receiver body in the length-direction, and this hermetic-sealing joint 111F can be adhered to the surface of a leak-proof part 22F opposite of the air-impermeable sheet 21.

What is claimed is:

1. A urine receiver which is implemented in a urine collection processing system which sucks urine discharged from a wearer into a urine tank via a urethral tube comprising, at the least:

an air-permeable sheet having liquid permeable characteristics sheet which is adapted to be placed opposite of and covering the urethral meatus of the wearer;

a leak-proof part which is placed on the surface of the air-impermeable sheet opposite to the urethral meatus and bonds to the outer border of the air-impermeable sheet;

a suction part which is provided between the air-impermeable sheet and the leak-proof part containing a space retention member, and into which the urethral tube is placed; and a sealing element for sealing the space between the air-impermeable sheet and the wearer's skin surface which is provided on the outer border part of the air-impermeable sheet on the urethral meatus side, wherein the space retention member includes a plurality of space retention materials, and wherein each space retention material has an essentially spherical shape and a diameter of about 2 mm to about 10 mm.

2. The urine receiver according to claim 1 wherein the sealing element is formed by a barrier-cuff which can rise up against the air-impermeable sheet.

3. The urine receiver according to claims 1 wherein the sealing element comprises an adhesive layer on free end sides which can be affixed to the skin of the wearer.

4. The urine receiver according to claim 1 wherein the sealing element comprises a first gathers which is elastic and expands along the length-direction of the suction part, and this first gathers rises up against the suction part by expanding and contracting.

5. The urine receiver according to claim 4 wherein the sealing element comprises a second gathers which is elastic and expands along the width-direction of the suction part.

6. The urine receiver according to claim 1 wherein the sealing element can rise up in an inverted funnel-shape towards the wearer.

7. The urine receiver according to claim 1 comprising: a liquid-permeable surface material part provided on the surface on the urethral meatus side of the air-impermeable sheet; and a back sheet part which covers the side of the leak-proof part opposite of the air-impermeable sheet.

8. The urine receiver according to claim 1 comprising at least one pair of electrodes placed on the surface of the urethral meatus side of the air-impermeable sheet, wherein urine can be detected by these electrodes becoming electrically conductive.

9. The urine receiver according to claim 1 wherein the leak-proof part is cup-shaped.

10. A urine collection processing system for suctioning urine discharged from a wearer into a urine tank via a urethral tube comprising:

a urine receiver which is implemented in a urine collection processing system which sucks urine discharged from a wearer into a urine tank via a urethral tube comprising, at the least:

an air-permeable sheet having liquid permeable characteristics which is adapted to be placed opposite of and covering the urethral meatus of the wearer;

a leak-proof part which is placed on the surface of the air-impermeable sheet opposite to the urethral meatus and bonds to the outer border of the air-impermeable sheet;

a suction part which is provided between the air-impermeable sheet and the leak-proof part containing a space retention member, and into which the urethral tube is placed, the space retention member including a plurality of space retention materials, each space retention material having an essentially spherical configuration with a diameter of about 2 mm to about 10 mm; and a sealing element for sealing the space between the air-impermeable sheet and the wearer's skin surface which is provided on the outer border part of the air-impermeable sheet on the urethral meatus side; and a urine tank which is connected to this urine receiver via a urethral tube; and a vacuum pump which sucks out urine received by the urine receiver by suctioning the air within the urine tank and collecting urine within the urine tank.

11. A urine receiver according to claim 1, further comprising a sensor for sensing the presence of urine, and a pump operatively connected therewith, the pump being configured to be responsive to the detection of urine by the sensor to pump urine from the urine receiver and deliver it to the urine tank via the urethral tube.

12. A urine receiver according to claim 11, wherein the sensor comprises a pair of electrodes disposed proximate the air-impermeable sheet, the electrodes being space and configured so that urine which collects between the electrodes can be detected though electrical continuity.

13. A urine collection processing system according to claim 10, further comprising a sensor for sensing the presence of urine, the vacuum pump being configured to be responsive to the detection of urine by the sensor and to pump urine from the receiver to the urine tank via the urethral tube.

14. A urine receiver according to claim 13, wherein the sensor comprises a pair of electrodes disposed proximate the air-impermeable sheet, the electrodes being space and configured so that urine which collects between the electrodes can be detected though electrical continuity.

* * * * *